United States Patent [19]

Black, deceased

[11] Patent Number: 4,708,241

[45] Date of Patent: Nov. 24, 1987

[54] SUTURE PACKAGE

[75] Inventor: Seymour Black, deceased, late of West Hartford, Conn., by Elizabeth Black, executrix

[73] Assignee: American Cyanamid Company, Stamford, Conn.

[21] Appl. No.: 893,853

[22] Filed: Aug. 6, 1986

[51] Int. Cl.[4] .............................................. A61L 17/02
[52] U.S. Cl. .................................... 206/63.3; 206/227; 206/380; 206/438
[58] Field of Search ...................... 206/63.3, 363, 380, 206/383, 438, 491, 227

[56] References Cited

U.S. PATENT DOCUMENTS

| 3,363,751 | 1/1968 | Shave et al. | 206/63.3 |
| 3,759,376 | 8/1973 | Lisowski | 206/63.3 |
| 3,857,484 | 12/1974 | Thyen | 206/227 |
| 4,063,638 | 12/1977 | Marwood | 206/63.3 |
| 4,069,912 | 1/1978 | Black et al. | 206/63.3 |
| 4,120,395 | 10/1978 | Mandel et al. | 206/63.3 |
| 4,135,623 | 1/1979 | Thyen | 206/63.3 |
| 4,406,363 | 9/1983 | Aday | 206/63.3 |
| 4,412,613 | 11/1983 | Kubas | 206/63.3 |
| 4,413,727 | 11/1983 | Cerwin et al. | 206/63.3 |

Primary Examiner—Stephen Marcus
Assistant Examiner—David T. Fidei
Attorney, Agent, or Firm—Charles F. Costello, Jr.

[57] ABSTRACT

A surgical suture package is disclosed. The package is self-contained and permits direct dispensing of one or more sutures.

1 Claim, 8 Drawing Figures

SUTURE PACKAGE

BACKGROUND AND SUMMARY OF THE INVENTION

This invention relates to a surgical suture package. The package is self-contained and permits direct dispensing of one or more sutures.

The significance of packaging is most evident in the packaging of surgical sutures. It is essential that the package protect the product, and maintain sterility throughout its period of potential use. Sutures may be stored in hospitals for several years, although the usual storage time is much shorter. It is also essential that the package provide rapid and positive means of identification, and release of the undamaged product, ready for use by the surgeon.

There are many sizes of sutures, and many materials of construction such as catgut or polyglycolic acid for absorbables and silk, cotton, nylon, polyethylene, polyethylene terephthalate, polypropylene, stainless steel, insulated stainless steel and other materials for use as non-absorbables. There are several different needle types in common use including pointed straight, pointed curved, three cornered straight, three cornered curved, curved both regular and reverse cutting, and needles with side cutting edges of various types. The variations and combinations of each of the above, to meet the preferences of many surgeons for different operative procedures, means that the suture manufacturer needs to supply different suture package combinations. These suture package combinations can run into the thousands. The importance of positive identification while maintaining an efficient, economical package can thus be readily appreciated.

It is also important to provide convenience to the surgeon and to limit the risk of accidently enclosing foreign items in the patient by limiting the number of extraneous packaging materials associated with use of the product in the operating theater. A count is often kept to ensure that each item is accounted for and removed from the operating field. Considering the ramifications of accidentally enclosing such material in the patient during surgical procedures, it is absolutely essential to minimize this hazard.

Finally, it is essential in a package containing a surgical needle or needles, that the suture is protected from contact with the sharp point or cutting edge of the needle, which could patially cut the suture or the package. Also, the armed needle edges and point need to be protected to maintain their sharpness.

The prior art generally discloses a surgical suture or sutures packaged in a strippable outer envelope. Contained in the strippable outer envelope is an inner envelope or pouch which is sterile. The suture strand or strands have been formed into various configurations of coils and loops, and are contained in or on various retainers, cards, or reels within the inner envelope.

The suture is normally prepared for the surgeon by stripping the outer envelope and transferring the inner envelope by sterile forceps, or by projecting it across a sterile barrier, into the sterile area of the operating room. The sterile inner envelope is then opened at the time of use.

The package of the present invention has advantages over the prior art. After stripping the outer envelope, the card containing the sutures is exposed. The sutures can then be directly dispensed without opening the card.

Another advantage is that the self-contained suture card can be printed with complete suture and needle identification. Special ink effects, e.g. stripping and coloring used in the printing, allows a color coding description of the suture and/or needle material for ease of identification.

The surgical suture card described above is enclosed in an envelope. At least one web of the envelope is a clear (transparent) material which allows full visibility of the descriptive literature on the card.

The envelope is sealed by methods known in the art, e.g. by heat sealing.

An improved surgical suture package containing multiple surgical suture strands has been invented. The package comprises a panel; a flap adjacent and foldably connected to one side of the panel; a foam layer contained on the coordinating surfaces of the panel and flap; and at least two surgical suture strands contained by the foam layer, with one end of the strands being external to the panel and flap. The improvement comprises a foam receptacle adjacent to the external end of the strands.

In one embodiment, the receptacle contains a plurality of slits, the number of slits essentially equal to or greater than the number of suture strand ends external to the improved package panel and flap. In another embodiment, the external end of each strand is needled.

In still another embodiment, the receptacle is contained on the improved package flap. In yet another embodiment, the receptacle is contained on the improved package panel. In a further embodiment, a score line foldably connects the flap to the panel.

In a still further embodiment, a self-contained package has been invented wherein at least one external edge of the improved package panel and flap contains a locking slit.

An improved direct dispensing surgical suture package containing multiple surgical suture strands has also been invented. The package comprises a first member having a first panel; a first flap adjacent and foldably connected to one side of the first panel; a foam layer contained on the coordinating surfaces of the first panel and flap; and at least two surgical suture strands contained by the foam layer, one end of the strands being external to the first panel and flap.

The package comprises a second member having a second panel; a second flap foldably connected to one side of the second panel, with the first member contained by the second member. The improvement comprises a foam receptacle contained on the second member adjacent to the external end of the strands whereby the end of each strand is contained by the receptacle.

In one embodiment, the receptacle contains a plurality of slits. The number of slits are essentially equal to or greater than the number of suture strand ends external to the first panel and flap. In another embodiment the external end of each strand is needled.

In still another embodiment, the receptacle is contained on the improved second flap. In a further embodiment, a self-contained package has been invented, wherein at least the second flap contains means for locking the second flap to the second panel.

A two part, direct dispensing, sterile surgical suture package has been invented. The first part comprises a panel; a flap adjacent and foldably connected to one side of the panel; a foam layer contained on the coordinating surfaces of the panel and flap; at least two surgical suture strands contained by the foam layer, one end of the strands external to the panel and flap; and a foam receptacle adjacent to the external end of the strands. The second part comprises a strippable envelope. The package first part is contained within the package second part.

A three part direct dispensing, self-contained, sterile surgical suture package has also been invented. The first part comprises a first panel; a first flap adjacent and foldably connected to one side of the first panel; a foam layer contained on the coordinating surfaces of the first panel and flap; and at least two surgical suture strands contained by the foam layer with one end of the strands being external to the first panel and flap.

The second part comprises a second panel; a second flap foldably connected to one side of the second panel; a foam receptacle contained on the second part adjacent to the external end of the strands, with each strand contained by the receptacle; and at least the second flap containing means for locking the second flap to the second panel.

The third part comprises a strippable envelope. The package first part is contained by the second part, and the second part is contained within the package third part.

In one embodiment the second part receptacle contains a plurality of slits. The number of slits is essentially equal to or greater than the number of suture strand ends external to the first panel and flap. In another embodiment, the external end of each strand is needled.

DETAILED DESCRIPTION

Figure 7:
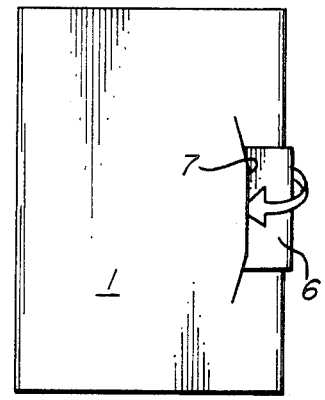
FIG. 7 is a back view showing a means for loading an edge of an exterior second side flap to the exterior panel.
Figure 8:
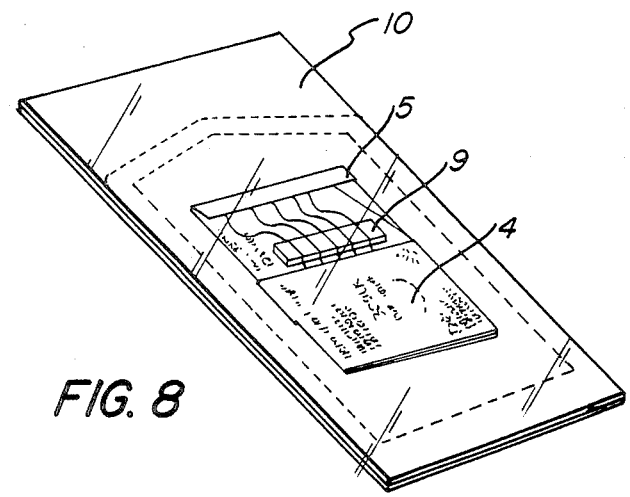
FIG. 8 is a perspective view showing the preferred loading of the suture card into a strippable envelope having at least one transparent side.

Referring to FIGS. 7 & 8, the suture card is and remains before, during and after its use a single piece. Referring specifically to FIG. 8, the needled suture ends are exposed at all times ready for single direct dispensing.

Figure 4:
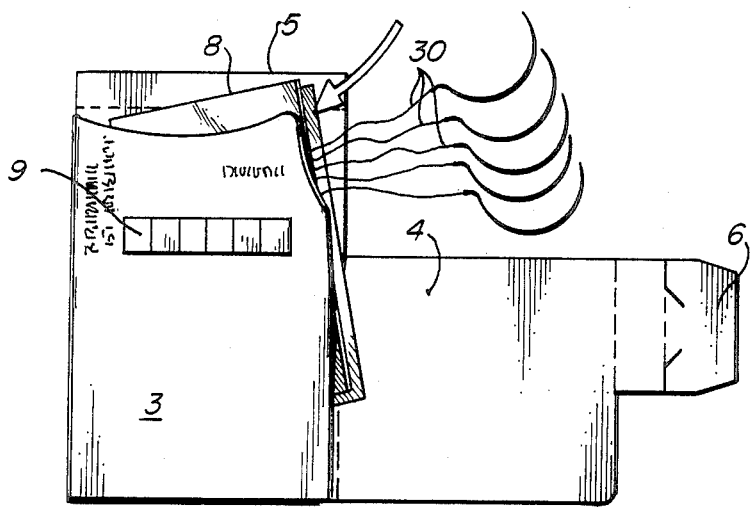
FIG. 4 is a front view showing the preferred orientation of the interior portion of the suture card in the exterior portion.
Figure 6:
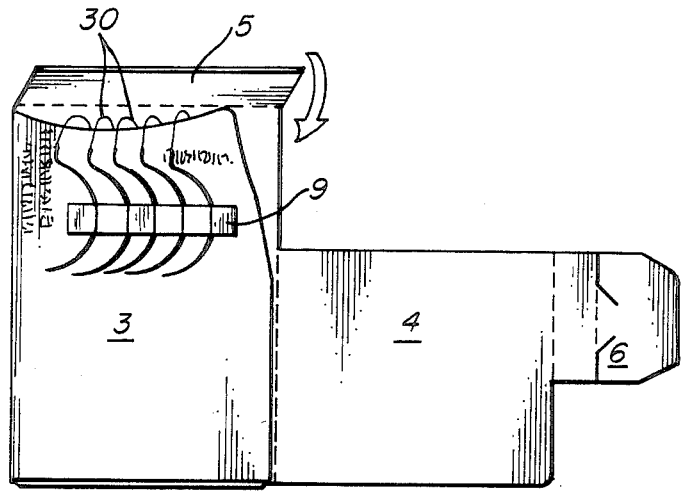
FIG. 6 is a front view showing the individual placement of the needled strand ends in the foam receptacle slits, and the folding of the optional top flap onto the first side flap.

Referring to FIGS. 4 and 6, the needled strand ends 30 can be lifted with the hand or with a needle holder. Each suture strand end 30 has its own position in the slit foam block 9, allowing individual unobstructed dispensing. Replacement of the needled strand ends 30 in the slits after use allows the user to maintain an exact count of the sutures used.

Referring to FIGS. 1 to 4, when the sutures are needled, a five piece exterior card 1 to 5 is designed to protect the strands from damage by the needle. Retention slits are located in the foam block 9 and a top folded flap 5 maintains the sutures within the card. The size and orientation of the slits assist to hold the needle in proper orientation, and to aid the grasping and dispensing of the needle with needle holders. Alternatively, the retention slits in the foam block 9 can be used with non-needled sutures.

Figure 1:
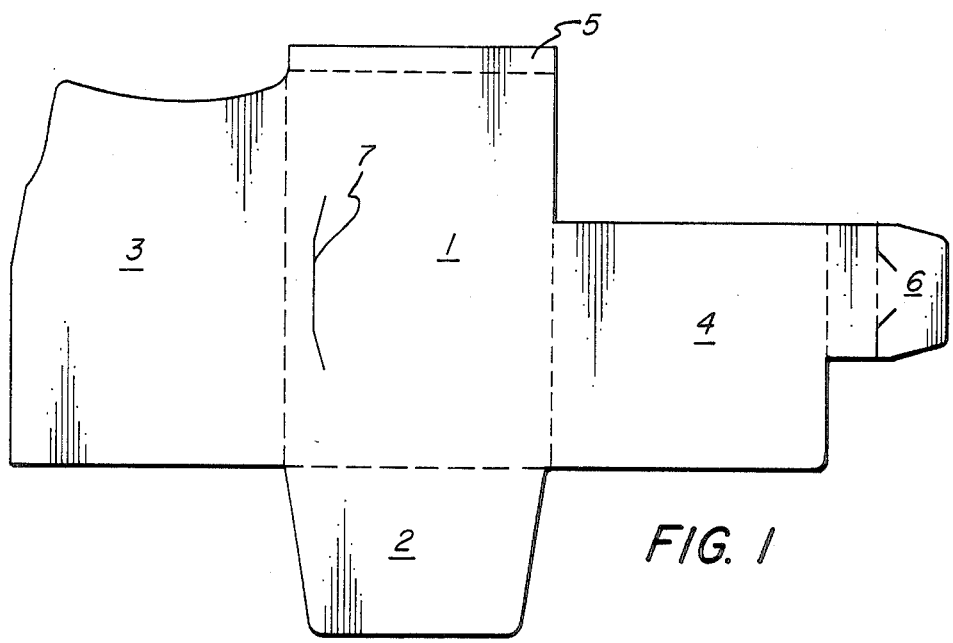
FIG. 1 is a front view of the exterior portion of the suture card.
Figure 2:
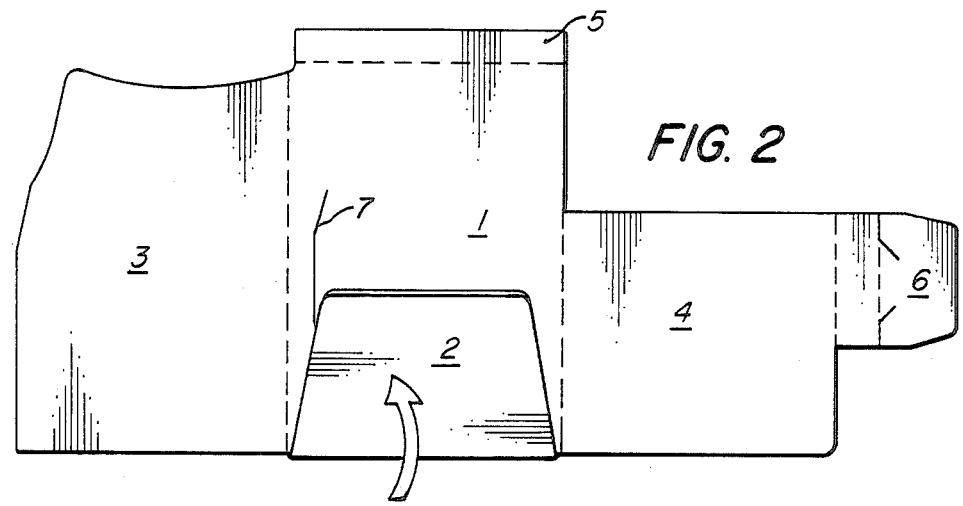
FIGS. 2 and 3 are front views showing the preferred folding sequence of the optional bottom flap (FIG. 2) onto the exterior panel and a first side flap (FIG. 3) onto the bottom flap.
Figure 3:
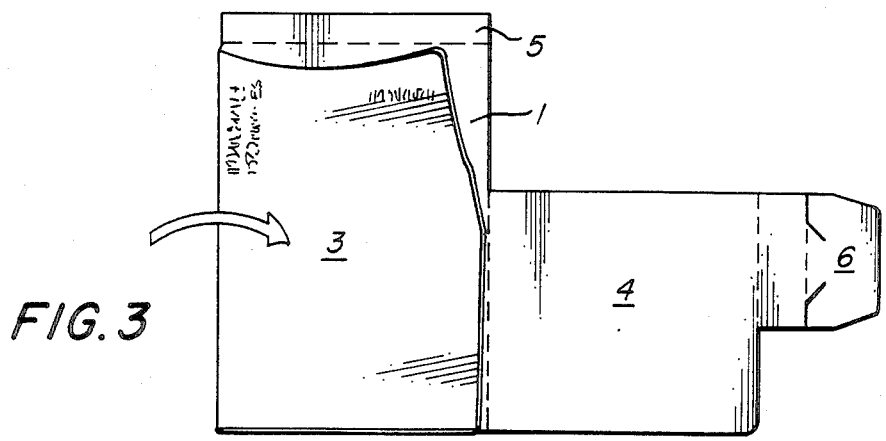
Figure 5:
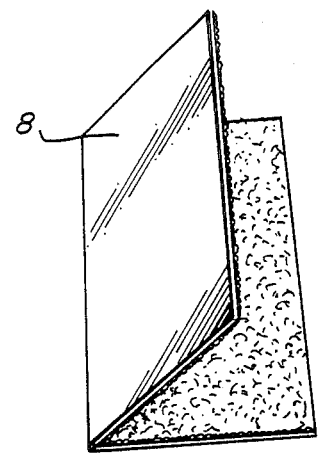
FIG. 5 is a schematic view showing the folding of the interior flap onto the interior panel.

The exterior card of FIGS. 1 to 3 and the interior card of FIG. 5 is preferably manufactured from a sterilizable paper of about 90 lb. weight, capable of withstanding alcoholic solutions, heat, steam, gas, or radiation sterilization without adverse effects. The paper may be coated with about ½ mil polyethylene so it is heat sealable. Such paper is known in the trade and is readily available. The foam layer contained on the coordinating surfaces of the interior card 8 shown in FIG. 5 is conventionally applied by methods known in the art. Sealing, if desired, may be by heat dies, or heat may be internally generated by ultrasonic means.

Referring to FIG. 8, the self-contained suture card of this invention can be used with a strippable outer envelope 10. The envelope material, the method of manufacturing the envelope material, and the method of loading the self-contained card of FIG. 7 into the envelope are well known in the suture packaging art.

The above described outer envelope material may also be used for the packaging of catgut sutures, which can be packaged with a desired quantity of alcohol solution to maintain plasticity. Some sutures, in which the moisture content is immaterial, may also be packaged in the same outer envelope material to maintain consistency of use and packaging standards.

The self-contained card of FIG. 7 can be loaded into a strippable envelope 10 of FIG. 8 as described in U.S. Pat. No. 4,069,912 entitled: "Suture Package" issued Jan. 24, 1978 to S. Black and D. C. MacRitchie, or U.S. Pat. No. 4,063,638 entitled "Direct Dispensing Packaging of Surgical Sutures" issued Dec. 20, 1977 to R. K. Marwood. These patents are incorporated herein by reference. Referring to FIG. 8, the strippable envelope 10 is peeled off. This action exposes at least the top cover flap 5 and the foam receptacle 9.

Referring to FIGS. 7 and 8 of this invention, the suture card is self-contained. Further, after all the sutures are dispensed, the card continues to be intact and in one piece. Thus no additional materials or articles other than the surgical suture strands are added to the operating area. Related hazards are thus minimized and accountability is simplified by replacing the needle in the slot foam block.

FIG. 1 shows a preferred exterior suture card. The exterior card is cutout and scored from a sheet of sterilizable paper, which may be coated with polyethylene for heat sealing by a method known in the art. The card consists of a back panel 1 to which is attached a first and second side flap 3 and 4, and a bottom and top flap 2 and 5. An extension of the second side flap 4 contains a locking tab 6. The tab 6 is placed into the retaining slit 7, as shown in FIG. 7, and after the folding sequence shown in FIGS. 2, 3, and 6.

Referring to FIG. 6, for a curved needle, the desired orientation is usually such that the arc of travel from the butt to the point is in a clockwise direction. This orientation is sometimes termed a right hand orientation because on dispensing, the needle is properly presented for a right handed user. The needles are thus embedded in the foam receptacle 9 with a right hand orientation. Alternatively, if the suture strand ends 30 are non-needled, they can be placed in the slits of the foam block 9.

FIGS. 2 to 7 show the preferred folding and self-containing of the exterior card. Specifically, FIG. 2 shows a bottom flap 2 folding onto the panel 1, and FIG. 3 shows a first side flap 3 folded onto the flap 2 and partially onto the panel 1.

Referring specifically to FIGS. 4 to 6, the ends of the suture strands 30 are shown in the appropriate positions during loading of the interior card 8 into the exterior card. The optional second side flap 4 can then be folded onto the first side flap 4.

The configuration of the strands contained in the coordinating surfaces of the interior card 8 can be any series of loops or coils that allow an individual strand to be dispensed freely from the self-contained package without tangling.

FIG. 7 shows a means for self-containing the interior and exterior cards. That is, a tab lock 6 is inserted into the slit 7 of panel 1 to provide a self-contained package. Finally, the side flap 4 is an aid in keeping the needles properly oriented and positioned in the self-contained package during processing or transit.

What is claimed:

1. A three part, direct dispensing, self-contained, sterile surgical suture package, the first part comprising:
   a first panel;
   a first flap adjacent and foldably connected to one side of said first panel;
   a foam layer contained on the coordinating surfaces of said first panel and flap; and
   at least two surgical suture strands contained by said foam layer, one end of said strands being external to said first panel and flap, wherein the external end of each strand is needled,
the second part comprising:
   a second panel;
   a second flap foldably connected to one side of said second panel;
   a foam receptacle contained on said second part adjacent to the external end of said strands, each strand contained by said receptacle;
   a plurality of slits contained on said receptacle, the number of slits essentially equal to or greater than the number of suture strand ends external to said first panel and flap; and
   at least said second flap containing means for locking said second flap to said second panel; and the third part comprising:
   a strippable envelope, said package first part contained by said second part and said second part contained within said package third part..

* * * * *